US012753416B2

(12) United States Patent
Guo et al.

(10) Patent No.: US 12,753,416 B2
(45) Date of Patent: Oct. 6, 2026

(54) BROAD-SPECTRUM DISEASE RESISTANCE-RELATED PROTEIN DERIVED FROM WHEAT AND RELATED BIOMATERIAL AND USE THEREOF

(71) Applicant: Northwest A&F University, Xianyang City (CN)

(72) Inventors: Jun Guo, Xianyang City (CN); Yanfeng Wang, Xianyang City (CN); Yuanyuan Du, Xianyang City (CN); Xingxuan Bai, Xianyang City (CN); Jia Guo, Xianyang City (CN); Yuanyang Qin, Xianyang City (CN); Zhensheng Kang, Xianyang City (CN)

(73) Assignee: NORTHWEST A&F UNIVERSITY, Xianyang City (CN)

( * ) Notice: Subject to any disclaimer, the term of this patent is extended or adjusted under 35 U.S.C. 154(b) by 299 days.

(21) Appl. No.: 18/482,239

(22) Filed: Oct. 6, 2023

(65) Prior Publication Data

US 2025/0019718 A1 Jan. 16, 2025

(30) Foreign Application Priority Data

Jul. 10, 2023 (CN) ......................... 202310840421.4

(51) Int. Cl.
*C12N 15/82* (2006.01)
*C07K 14/415* (2006.01)

(52) U.S. Cl.
CPC ........ *C12N 15/8282* (2013.01); *C07K 14/415* (2013.01)

(58) Field of Classification Search
CPC .......................... C12N 15/8282; C07K 14/415
See application file for complete search history.

(56) References Cited

PUBLICATIONS

GenBank reference KAE8768415.1: https://www.ncbi.nlm.nih.gov/protein/KAE8768415.1?report=genbank&log$=prottop&blast_rank=1&RID=B0VUFDAK015 (Year: 2019).*
UniProt entry A0A3B6MSE5_WHEAT: https://www.uniprot.org/uniprotkb/A0A3B6MSE5/entry (Year: 2018).*
Guo et al (2018) Front. Plant Sci. 9:18. (Year: 2018).*
EnsemblPlants region Chromosome5D 343, 118,048-343, 120,601: https://plants.ensembl.org/Triticum_aestivum/Location/View?db=core;g=TraesCS5D02G235100;r=5D:343118048-343120601;t=TraesCS5D02G235100.1 (Year: 2025).*
(Continued)

*Primary Examiner* — Anne Kubelik
*Assistant Examiner* — Victoria L Deleo
(74) *Attorney, Agent, or Firm* — Sydney E. McKinney; Moore & Van Allen PLLC

(57) ABSTRACT

A broad-spectrum disease resistance-related protein derived from wheat and related biomaterials and use thereof are provided. The protein is selected from the group consisting of A1) a protein with the amino acid sequence of SEQ ID NO: 1; A2) a protein having more than 80% identity to, having a same function as the protein with the amino acid sequence of SEQ ID NO: 1, and obtained by substitutions and/or deletions and/or additions of amino acid residues thereof, and A3) a fusion protein with a same function obtained by joining a tag at N-terminus and/or C-terminus of A1) or A2). The TaCNGC5.1 overexpression lines showed significantly improved disease resistance, thus suggesting that TaCNGC5.1 may play an important role in breeding plants with improved resistance to stripe rust.

1 Claim, 5 Drawing Sheets

Specification includes a Sequence Listing.

(56) References Cited

PUBLICATIONS

EnsemblPlants Transcript: TraesCS5D02G235100.1: https://plants.ensembl.org/Triticum_aestivum/Transcript/Sequence_cDNA?db=core;g=TraesCS5D02G235100;r=5D:343118048-343120601;t=TraesCS5D02G235100.1 (Year: 2025).*

Tsomin et al (1990) Euphytica. 48: 83-86. (Year: 1990).*

* cited by examiner

BROAD-SPECTRUM DISEASE RESISTANCE-RELATED PROTEIN DERIVED FROM WHEAT AND RELATED BIOMATERIAL AND USE THEREOF

CROSS-REFERENCE TO RELATED APPLICATION

This patent application claims the benefit and priority of Chinese Patent Application No. 2023108404214 filed with the China National Intellectual Property Administration on Jul. 10, 2023, the disclosure of which is incorporated by reference herein in its entirety as part of the present application.

REFERENCE TO SEQUENCE LISTING

A computer readable XML file entitled "HLP20230705716_seqlist", which was created on Nov. 19, 2025, with a file size of about 23,952 bytes, contains the sequence listing for this application, has been filed with this application, and is hereby incorporated by reference in its entirety.

TECHNICAL FIELD

The present disclosure belongs to the field of genetic engineering and specifically relates to a broad-spectrum disease resistance-related protein derived from wheat and a related biomaterial and use thereof.

BACKGROUND

Wheat stripe rust is a major disease of wheat caused by the wheat stripe rust fungus (*Puccinia stiiformis* f. sp. *tritici*), which is a serious hazard worldwide. China is the largest epidemic area of stripe rust in the world, with an average annual incidence of about 4 million hectares. After the stripe rust fungus infests into the host plant, the host plant develops symptoms such as yellow wilt and necrosis. Or when the fungus produces a large number of uredinia on the host surface, green leaves and tissues are reduced, resulting in a great reduction of photosynthesis in the plant.

In nature, plants have evolved sophisticated defense mechanisms against pathogenic microbes. These defense mechanisms include PAMP-triggered immunity (PTI) and effector-triggered immunity (ETI). ETI is usually accompanied by the onset of hypersensitive response (HR). HR is the most common form of disease resistance in plants, as evidenced by the formation of localized dieback at the point of infestation and limitation of pathogen growth. Because MAMPs, PAMPs or DAMPs are much conserved, PTIs are readily recognized by most pathogens, whereas effector proteins are highly specific, resulting in differences in ETIs between species or physiological races. Although the activation of ETI and PTI differ in their modes of activation, both induce a range of plant immune responses, including ion mobility at lipid membranes, an increase in intracellular calcium ion concentration, formation of reactive oxygen species (ROS), and activation of the mitogen-activated protein kinase (MAPK) signaling pathway. Subsequent reactions include secretion of antimicrobial proteins, lignification of the cell wall, and so on.

Therefore, it has become an important tool for the sustainable control of wheat stripe rust to improve the disease resistance of wheat through mining wheat disease resistance genes, and understanding the response and signaling mechanisms of wheat under stripe rust stress.

BRIEF SUMMARY

The technical problem to be solved by the present disclosure is to provide a wheat disease resistance protein. The technical problem to be solved is not limited to the described technical subject matter, and other technical subject matters not mentioned herein will be clearly understood by those skilled in the art according to the following description.

To solve the above technical problem, the present disclosure provides the following technical solution.

The present disclosure provides use of a protein, a substance regulating expression of a gene encoding the protein, or a substance regulating activity and/or content of the protein in the following aspects of D1)-D6).

The protein is named as TaCNGC5.1 and is selected from the group consisting of

A1) a protein with the amino acid sequence of SEQ ID NO: 1;

A2) a protein having more than 80% identity to, having a same function as the protein with the amino acid sequence of SEQ ID NO: 1, and obtained by substitutions and/or deletions and/or additions of amino acid residues thereof, and A3) a fusion protein with a same function obtained by joining a tag at N-terminus and/or C-terminus of the protein of A1) or A2);

D1-D6 are as follows:

D1) increasing disease resistance in wheat;

D2) preparation of a products to improve disease resistance in wheat;

D3) breeding wheat with improved disease resistance;

D4) preparation of a product for breeding wheat with improved disease resistance;

D5) improving wheat with high disease resistance or preparation of a product of wheat with high disease resistance; and D6) breeding wheat.

The protein provided by the present disclosure is derived from the wheat variety Suwon 11 (*Triticum aestivum*).

In order to facilitate the purification or assay of the protein in A1), protein tags may be attached to the amino terminus or carboxy terminus of the protein with the amino acid sequence listed in Table 1.

TABLE 1

Sequences of protein tags

| Tag | Residue | Sequence | SEQ ID NO: |
|---|---|---|---|
| Poly-Arg | 5-6 (usually 5) | RRRRR | 15 |
| Poly-His | 2-10 (usually 6) | HHHHHH | 16 |
| FLAG | 8 | DYKDDDDK | 17 |
| Strep-tag II | 8 | WSHPQFEK | 18 |
| c-myc | 10 | EQKLISEEDL | 19 |

The protein TaCNGC5.1 in A2) may be synthesized artificially, or the gene encoding the protein may be synthesized first and then biologically expressed to obtain the protein. The gene encoding the protein TaCNGC5.1 in A2) may be obtained by deletion and/or missense mutation of the DNA sequence set forth in SEQ ID NO: 1, and/or by ligation of the coding sequence with the tag shown in Table 1 at its 5' end and/or 3' end.

The nucleotide sequence encoding TaCNGC5.1 of the present disclosure can be easily mutated by one of ordinary skill in the art using known methods, such as directed evolution and point mutation. Those nucleotides that have been artificially modified to have 75% or greater identity to the nucleotide sequence of TaCNGC5.1 isolated and obtained from the present disclosure are derived from and equivalent to the nucleotide sequence of the present disclosure as long as they encode TaCNGC5.1 and have the same function.

The term "identity" as used herein refers to sequence similarity relative to a natural nucleic acid sequence. Nucleotide sequences having an "identity" includes those having at least 75%, at least 85%, at least 90%, or at least 95% identity to the nucleotide sequence of a protein with the amino acid sequence of SEQ ID NO: 1 of the present disclosure. The identity can be evaluated by naked eyes or by computer software. In computer software, the identity between two or more sequences can be expressed as a percentage (%), which can be used to evaluate the identity between related sequences.

The at least 75% identity may be at least 80%, 85%, 90%, or 95% identity.

Regulating the expression of the gene coding for protein TaCNGC5.1 may be enhancing, up-regulating or increasing the expression of the gene coding for protein TaCNGC5.1. Regulating protein activity and/or content of protein TaCNGC5.1 may be enhancing, up-regulating or increasing the activity and/or content of protein TaCNGC5.1.

The disease resistance in wheat refers to resistance to stripe rust. The stripe rust can be caused by infection with at least one of the pathogens selected from stripe rust physiological race group consisting of CYR31, CYR32, CYR33 and CYR34.

The substances described above are biomaterials selected from the group consisting of B1) a nucleic acid molecule encoding the protein;

B2) an expression cassette containing the nucleic acid molecule in B1);

B3) a recombinant vector containing the nucleic acid molecule in B1), or a recombinant vector containing the expression cassette in B2); and B4) a recombinant microorganism containing a nucleic acid molecule described in B1), or a recombinant microorganism containing an expression cassette described in B2), or a recombinant microorganism containing a recombinant vector in B3);

B5) a transgenic plant cell line containing the nucleic acid molecule in B1), or a transgenic plant cell line containing the expression cassette in B2);

B6) a transgenic plant tissue containing the nucleic acid molecule in B1), or a transgenic plant tissue containing the expression cassette in B2); and B7) a transgenic plant organ containing the nucleic acid molecule in B1), or a transgenic plant organ containing the expression cassette in B2);

where, the nucleic acid molecule in B1) is a cDNA molecule or a DNA molecule with a coding sequence of SEQ ID NO: 2, encoding the amino acid sequence set forth in SEQ ID NO: 1.

In the biomaterials, the expression cassette containing the nucleic acid molecule encoding TaCNGC5.1 (TaCNGC5.1 gene expression cassette) refers to a DNA capable of expressing TaCNGC5.1 in a host cell, and may include not only a promoter for initiating the transcription of TaCNGC5.1, but also a terminator for terminating the transcription of TaCNGC5.1. Further, the expression cassette may also include an enhancer sequence. Promoters that may be used in the present disclosure include, but are not limited to: constitutive promoters; tissue-, organ- and development-specific promoters and inducible promoters. Suitable transcriptional terminators include, but are not limited to the nopaline synthase terminator (NOS terminator), the cauliflower mosaic virus (CaMV) 35S terminator, the tml terminator, the pea rbcS E9 terminator, and the mannopine synthase (Mas) or octopine synthase (Ocs) terminators.

Recombinant vectors containing the TaCNGC5.1 gene expression cassette can be constructed with expression vectors in the art. The plant expression vectors include, for example, binary *Agrobacterium* vectors and vectors that can be used for plant particle bombardment, such as pAHC25, pBin438, pCAMBIA1302, pCAMBIA2300, pCAMBIA2301, pCAMBIA1305, pCAMBIA1300, ZpBI121, pCAMBIA1391-Xa, or pCAMBIA1391-Xb (CAMBIA Corp.). The expression vectors for plant may also include a 3'-end non-translated region of an exogenous gene, i.e., including a polyadenylate signal and any other DNA fragment involved in mRNA processing or gene expression. The polyadenylate signal directs the incorporation of polyadenylate into the 3' end of the mRNA precursor, for example, both *Agrobacterium* crown gall tumor-inducing (Ti) plasmid genes (e.g., the nopaline synthase gene, Nos), and the non-translated region of transcription at the 3' end of plant genes (e.g., the embryonic storage protein genes) have such similar functions. When plant expression vectors are constructed using the genes of the present disclosure, enhancers, including translational enhancers and transcriptional enhancers, may also be used, and these enhancer regions may include ATG start codons or neighboring region start codons, etc., provided that it has the same reading frame as that of the coding sequence in order to ensure the correct translation of the entire sequence. The sources of the translation control signals and start codons are wide-ranging and can be natural or synthetic. Translation initiation regions can be derived from transcription initiation regions or structural genes. In order to facilitate the identification and screening of transgenic plant cells or plants, the plant expression vectors used may be processed, e.g., by incorporating genes encoding enzymes or luminescent compounds that produce color changes (GUS genes, luciferase genes, etc.), marker genes for antibiotics (such as the nptII gene conferring resistance to kanamycin and related antibiotics, the bar gene conferring resistance to the herbicide phosphinothricin, the hph gene conferring resistance to the antibiotic hygromycin, the dhfr gene conferring resistance to methotrexate, and the EPSPS gene conferring resistance to glyphosate), or chemical marker genes such as those conferring resistance to phytocide, or the mannose-6-phosphate isomerase gene having the ability to metabolize mannose. In view of the safety of transgenic plants, transformed plants can be directly screened under stress without adding any selective marker gene.

In the biological biomaterials, the vector may be a plasmid, a cosmid, a phage or a viral vector.

In the biomaterials, the microorganism may be yeast, bacteria, algae or fungi, such as *Agrobacterium.*

In the biomaterials, none of the transgenic plant cell lines is for propagation.

The present disclosure also provides a method for breeding transgenic wheat with improved disease resistance, including up-regulating or enhancing or increasing the expression of a gene encoding the foregoing protein or the content of the protein in target wheat to obtain disease-resistant wheat having higher disease resistance than the target wheat.

Disease resistance of the wheat in the method is resistance to stripe rust. The stripe rust can be caused by infection with at least one of the pathogens selected from stripe rust physiological race group consisting of CYR31, CYR32, CYR33 and CYR34. The resistance to stripe rust is specified in any one of the following (1)-(3): (1) the spore production of the stripe rust bacteria infesting the transgenic wheat is lower than that of the recipient plant under the stripe rust stress conditions; (2) the expression level of the disease course-related genes of the transgenic plant is higher than that of the recipient plant under the stripe rust stress conditions; and (3) the area of the stripe rust mycelium infestation of the stripe rust fungus infesting the transgenic wheat is lower than that of the recipient plant under the stripe rust stress conditions. The stripe rust stress conditions are compatible or incompatible treatments, with CYR31 strain for compatible treatment and CYR23 strain for incompatible treatment.

The wheat is specifically the wild type wheat Fielder.

Up-regulating, enhancing or increasing the expression of the gene encoding the protein or the content of the protein in the target wheat in the method is to introduce the gene encoding the protein into the target wheat.

In an embodiment of the present disclosure, the gene encoding the TaCNGC5.1 protein (i.e., the nucleotide of SEQ ID NO: 2) is introduced into *Agrobacterium tumefaciens* EHA105 by means of a recombinant vector CUB-TaCNGC5.1 containing an expression cassette for the gene encoding the TaCNGC5.1 protein. The recombinant vector CUB-TaCNGC5.1 is introduced into *Agrobacterium tumefaciens* EHA105 by homologous recombination to insert a DNA fragment of TaCNGC5.1 into the CUB vector while keeping the other sequences of the CUB vector intact. The vector cleavage site is BamHI.

In the above method, the transgenic plant is understood to include not only the first generation of transgenic plants obtained by transforming the recipient plant with the TaCNGC5.1 gene, but also its progeny. In the case of transgenic plants, the gene can be propagated in the species or can be transferred into other varieties of the same species, including in particular commercial varieties, using conventional breeding techniques. The transgenic plants include seeds, callus, complete plants and cells.

The aforementioned proteins, the biomaterials in B1) to B4) also fall within the scope of the present disclosure.

The experiments of the present disclosure have demonstrated that the TaCNGC5.1 gene discovered in the present disclosure is induced to be expressed by *Puccinia striiformis* f. sp. *tritici*, and that the transgenic wheat obtained by introducing the TaCNGC5.1 gene into wheat is more resistant to multiple physiological races of *Puccinia striiformis* f. sp. *tritici* than the wild-type wheat. The proteins and genes provided by the present disclosure provide a basis for artificially controlling the expression of disease resistance-related genes, and will play an important role in breeding plants with broad-spectrum disease resistance.

DETAILED DESCRIPTION

Figure 1:
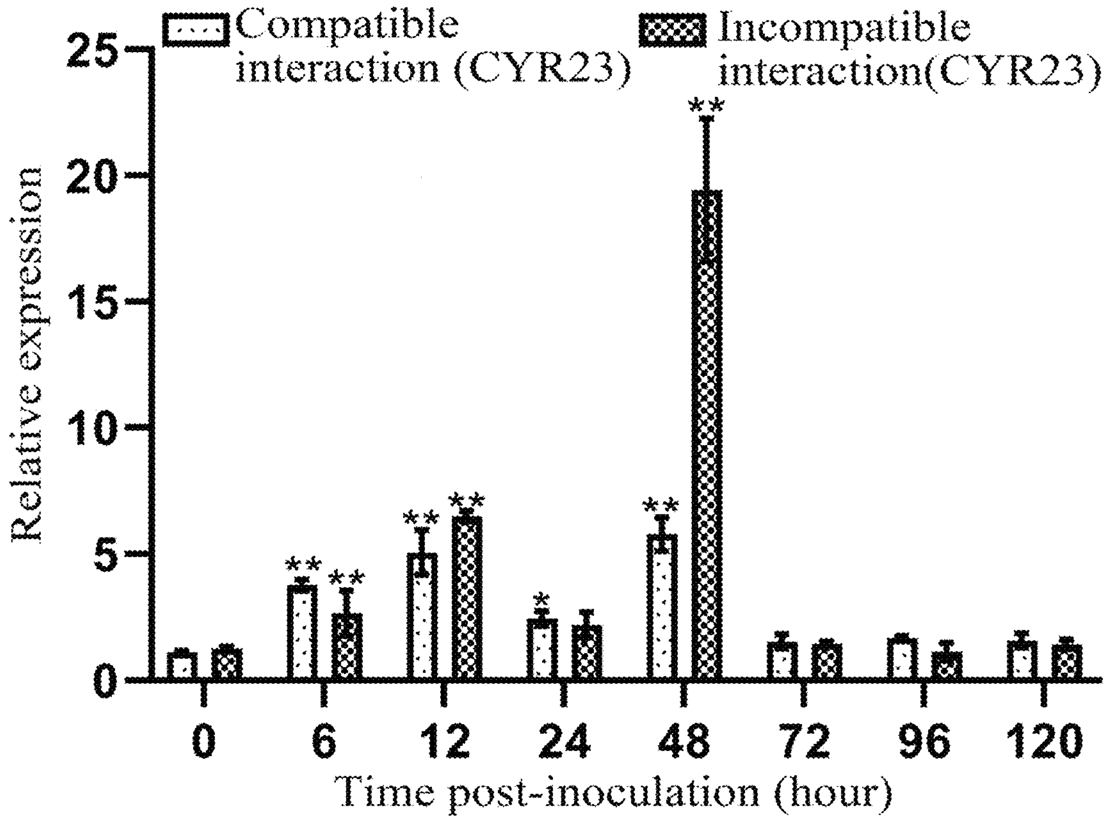
FIG. 1 shows the expression profile of TaCNGC5.1 in wheat and stripe rust mutualistic combinations.

The present disclosure is described in further detail below in conjunction with specific examples, which are given for the sole purpose of elucidating the present disclosure and not for the purpose of limiting the scope of the present disclosure. The examples provided below may serve as a guide for further improvements by a person of ordinary skill in the art, and do not in any way limit the present disclosure.

The experimental methods in the following examples, if not otherwise specified, are conventional methods, and are performed in accordance with the techniques or conditions described in the literature in the field or in accordance with the instructions for the product. The materials, reagents, and the like used in the following examples are commercially available, if not otherwise specified.

The GFP16318 (green fluorescent protein) vector in the following example is documented in the literature "Molecular characteristics and functional identification of foxtail millet transcription factor WRKY36 [J]. Scientia Agricultura Sinica, 2015, 48(5):851-860.", which is available to the public from the Northwest A&F University.

The wheat stripe rust physiological race CYR23 in the following example is described in the literature "Liu P, Guo J, Zhang R, et al. TaCIPK10 interacts with and phosphorylates TaNH2 to activate wheat defense responses to stripe rust[J]. Plant biotechnology journal, 2019, 17(5): 956-968.". It is available to the public from the Northwest A&F University.

The wheat variety Fielder, the wheat stripe rust physiological races CYR32, CYR33 and CYR34 in the following example are described in the literature "Bai X, Zhan G, Zhang R, Tian S, et al. Transcription factor BZR2 activates chitinase Cht20.2 transcription to confer resistance to wheat stripe rust [J]. Transcription factor BZR2 activates chitinase Cht20.2 transcription to confer resistance to wheat stripe rust [J]. Plant physiology, 2021, 187: 2749-2762.". They are available to the public from the Northwest A&F University.

The wheat stripe rust fungus CYR31 in the following example is described in the literature "Fengle Wang, Liren Wu, Shichang Xu, Shelin Jin, Qiuzhen Jia, Wenhuan Yuan, Jiaxiu Yang. The discovery and studies on new races CYR30 and CYR31 of wheat stripe rust in china [J]. Acta Phytophylacica Sinica, 1996(01):39-44.". It is available to the public from Northwest A&F University.

The wheat variety suwon 11 in the following example is described in the literature "Cao Zhangjun, Jing Jinxue, Wang Meinan, et al. Relation analysis of stripe rust resistance gene in wheat important cultivar suwon 11, suwon 92 and hybrid 46 [J]. Acta Botanica Boreali-Occidentalia Sinica, 2003, 23(1): 64-68." It is available to the public from Northwest A&F University.

Cellulase R10 (YaKult Honsha) cellulase (Yakult, C6270-1g), Mecerozyme R10 (YaKult Honsha) pectinase (Rongxing Biotechology, RX-L0042-100 mg), Mannitol (Beijing Mengyimei Trade Center, M0122-500g), KOH (Beijing Xiyanghuizhi Technology Co., Ltd, XYHZ-2017-05185), KCl (Beijing Biorj Science and Technology Co., Ltd, 7447-40-7), MES (Beijing BioDee Biotechnology Co., Ltd, DE-E169-100g), $CaCl_2$) (Beijing BioDee Biotechnology Co., Ltd, 031-00435), NaCl (Beijing BioDee Biotechnology Co., Ltd., 7647-14-5), $MgCl_2$ (Beijing BioDee Biotechnology Co., Ltd., DE-0288-500g), Glucose (Beijing BioDee Biotechnology Co., Ltd., 049-31165), PEG4000 (Beijing BioDee Biotechnology Co., Ltd., BR-0084), Bovine Serum Albumin (BSA, Beijing ZEPING Bioscience & Technology Co., Ltd, 0219989980), β-Mercaptoethanol (Beijing Readerbio technology Co., Ltd., 0482-100ML).

The formulations of the reagents used in the following examples are as follows.

TABLE 2

| Cellulose solution formulations | | |
|---|---|---|
| | Reagents | 15 ml cellulose solution system |
| 1 | Cellulase R10 (YaKult Honsha) cellulase | 0.225 g dry powder |
| 2 | Mecerozyme R10 (YaKult Honsha) pectinase | 0.045 g dry powder |
| 3 | Mannitol | 1.09 g dry powder |
| 4 | KCl | 1 ml of 0.3M KCl mother liquor |
| 5 | MES (213.2 g/mol), pH 5.7 | 1 ml of 0.3M MES, pH 5.7 masterbatch |
| 6 | | Add 10 ml of water (distilled water) |
| 7 | Heat at 55° C. in a water bath for 10 minutes, cool to room temperature and add the following reagents | |
| 8 | 10 mM $CaCl_2$ | 1 ml 0.15M $CaCl_2$ |
| 9 | BSA | 1 ml 1.5% BSA (stored at 4° C.) |
| 10 | β-mercaptoethanol | 5 μl |
| 11 | filter with 0.45 μm filter membrane | filtration |

TABLE 3

| PEG4000 solution | | |
|---|---|---|
| 1 | PEG4000 | 1 g |
| 2 | Water | 0.75 ml |
| 3 | 0.8M Mannitol | 0.625 ml |
| 4 | 1 M $CaCl_2$ | 0.25 ml |
| 5 | Approx. 1.2 ml | |

TABLE 4

| W5 solution W5 (1000 ml) | | |
|---|---|---|
| 154 mM NaCl | NaCl | 9 g |
| 125 mM $CaCl_2$ | $CaCl_2$ H $O_2$ | 18.4 g |
| 5 mM KCl | KCl | 0.37 g |
| 5 mM glucose | glucose | 0.9 g |
| 0.03% MES | MES | 0.3 g |

Adjust pH to 5.8 with KOH, autoclave for 20 minutes and store at room temperature.

TABLE 5

| MaMG solution MaMg solution (500 ml) | | |
|---|---|---|
| 15 mM $MgCl_2$ | $MgCl_2$ | 0.71 g |
| 0.1% MES | MES | 0.5 g |
| 0.4M Mannitol | Mannitol | 36.5 g |

Adjust pH to 5.6 with KOH, autoclave for 20 minutes and store at room temperature.

TABLE 6

| WI solution WI (200 ml) | | |
|---|---|---|
| 0.5M Mannitol | Mannitol | 18.217 g |
| 4 mM MES, pH 5.7 | MES | 0.3 g |
| 20 mM KCl | KCl | 0.12 g |

Autoclave and store at room temperature.

Example 1: Acquisition of TaCNGC5.1 Protein and the Gene Encoding the Protein

I. Isolation of mRNA and Amplification of TaCNGC5.1

Seedlings of normally grown 7-day-old wheat suwon 11 were taken, snap-frozen in liquid nitrogen and stored at −80° C. for later use.

Total RNA from wheat leaves was extracted using a Quick RNA isolation kit (Huayueyang Biotechnology (Beijing) Co., Ltd.), and the first-strand cDNA was synthesized with reverse transcriptase XL (AMV). The cDNA was synthesized by the Switching Mechanism at 5' End of RNA Template (SMART) method. PCR was carried out with the cDNA as a template, and TaCNGC5.1-F and TaCNGC5.1-R as primers. The PCR product was detected by 1.0% agarose gel electrophoresis, and a PCR product of 2070 bp was obtained. The amplification primers were:

```
TaCNGC5.1-F:
                                   (SEQ ID NO: 3)
5'-ATGGACGGCCCCGGCAGCGGCCACC-3';

TaCNGC5.1-R:
                                   (SEQ ID NO: 4)
5'-TTAGTCTTTTGGCTTGGGCAGCAGA-3'.
```

The PCR product was shown to have the nucleotide of SEQ ID NO: 2 in the sequence listing according to the sequencing results, which was named as TaCNGC5.1 gene. The gene encodes a protein with the amino acid sequence of SEQ ID NO: 1 in the sequence listing, and was named as TaCNGC5.1 protein.

```
(689AA)
                                    SEQ ID NO: 1
MDGPGSGHQMDSYFSRAPKIRSRSIRMAAAGVMSQSERLKNIGRRVFQED

LKSISLKIYDPQDPFLMRMNRLFVFACIISVATDPLFFYLPSVNVTQSNT

CIGFKRELAVAATAVRTAIDFFYLARIVLQFHTAFIAPSSRVFGRGELVV

DHGDIARRYLRRFFVVDLLSVLPLPQIQMYKFFMKPKNADLLPVKTALFF

NVLTQYLPRLLRFYPITAELRRTTGVFAETALSGAAFYLLLYMLCSHMVG

SFWYLLAVERLDDCWREKCAGLKFHQCRIYMYCGGKQEGDEDDFMKWRTM

IRQVLAQECAPVDNNGTGFSYGIYTSAMTSGVTHTNDLVPKILYCLWWGL

QNLSSGAQGLETTHYKGEALFAIILAVFGLILMALLIGNMQTYLQSMTLR

MEEMRLKRRDSEEWMRHRDLPDDLRERVWRHNQYKWLETRGVDEDGLVSC

LPKDIRRDVKRHLCLRLVRRVPLFANMDERLLDAICERLKPSLCTETTYV

VREGEPVDEMLFIIRGRLESSTTDGGRTGFFNKGLLKEGDFCGEELLTWA
```

-continued

LDPKAAANLPLSTRSVKALSEVEGFALHADELKFVAGQFRRLHSKQLQQT

FRFYSQQWRTWASCFIQAAWRRYEKRKAAEHRRREEEEMYAAEMVSASSS

SQIKTAFLVSRFAKNAMRGVQRQRSHQEERLILLPKPKD (2070bp)

SEQ ID NO: 2

ATGGACGGCCCCGGCAGCGGCCACCAGATGGACAGCTACTTCTCCCGCGC

CCCCAAGATCCGGTCCCGGTCCATCCGCATGGCGGCTGCCGGCGTGATGA

GCCAGTCGGAGCGGCTCAAGAACATCGGGCGCCGTGTCTTCCAGGAGGAC

CTTAAGAGCATCTCCCTCAAGATCTACGACCCGCAGGACCCGTTCCTGAT

GCGCATGAACCGCCTCTTCGTCTTCGCCTGCATCATCTCCGTCGCCACCG

ACCCGCTCTTCTTCTACCTCCCTTCCGTCAACGTGACCCAGAGCAACACA

TGCATCGGCTTCAAACGTGAACTGGCCGTCGCTGCCACCGCTGTGCGCAC

CGCCATCGACTTCTTCTACCTGGCGCGGATCGTGCTGCAGTTCCACACCG

CCTTCATCGCGCCGTCGTCGCGGGTGTTTGGCCGCGGGGAGCTCGTCGTC

GACCATGGTGACATAGCGCGCCGCTACCTCCGCCGTTTTTTCGTCGTCGA

CCTCCTCTCTGTGCTCCCCCTGCCACAAATCCAGATGTACAAGTTCTTCA

TGAAGCCCAAGAACGCGGACCTGCTTCCCGTCAAGACGGCGCTCTTCTTC

AACGTACTCACCCAGTACTTGCCCCGCCTCCTCCGCTTCTACCCTATCAC

CGCCGAACTCAGGCGCACCACCGGCGTCTTCGCAGAGACTGCCTTATCCG

GCGCCGCCTTCTACCTCCTCCTCTACATGCTATGCTCACACATGGTGGGT

TCCTTCTGGTACCTCCTCGCCGTCGAGCGCCTCGACGACTGCTGGCGCGA

GAAGTGCGCGGGGCTCAAGTTCCACCAGTGCAGGATATACATGTACTGCG

GGGGGAAACAAGAGGGCGATGAGGACGACTTCATGAAGTGGCGGACCATG

ATCCGGCAGGTGCTCGCGCAGGAGTGCGCGCCTGTGGACAACAACGGCAC

GGGCTTCAGCTACGGCATCTACACCTCCGCCATGACCTCAGGGGTCACCC

ACACCAACGACCTCGTCCCGAAGATTCTCTACTGCCTGTGGTGGGGTCTC

CAGAACCTCAGCAGTGGCGCCCAGGGGCTGGAGACCACGCACTACAAGGG

GGAGGCCCTTTTCGCCATCATCCTCGCGGTCTTCGGCCTCATCCTCATGG

CGCTGCTCATCGGCAACATGCAGACGTACCTCCAGTCCATGACGCTGCGT

ATGGAGGAGATGCGGCTCAAGCGGCGGGACTCGGAGGAGTGGATGCGCCA

TCGCGACCTCCCCGATGACCTCCGGGAGCGTGTGTGGCGACACAACCAGT

ACAAGTGGCTGGAGACGCGGGGCGTGGACGAGGACGGCCTTGTGAGCTGC

CTCCCCAAGGACATCCGGCGAGACGTCAAGCGCCACCTCTGCCTCCGCCT

CGTCCGCCGCGTGCCGCTCTTTGCCAACATGGACGAGCGCCTCCTCGACG

CCATCTGCGAGAGGCTCAAGCCCAGCCTATGCACGGAGACCACCTACGTG

GTGCGGGAAGGGGAGCCCGTCGACGAGATGCTCTTCATCATCAGAGGCCG

GCTCGAGAGTTCCACCACCGACGGGGGCCGCACGGGGTTCTTCAACAAGG

GGCTCCTCAAGGAAGGGGACTTCTGCGGCGAGGAGCTCCTCACATGGGCG

CTGGACCCAAAGGCTGCGGCGAACCTGCCGCTGTCCACTCGTAGTGTCAA

GGCGCTCTCCGAGGTGGAGGGCTTCGCGCTGCACGCCGATGAGCTTAAGT

TCGTCGCGGGGCAGTTCCGGCGCCTGCACAGCAAGCAATTGCAGCAGACC

-continued

TTCAGGTTCTACTCGCAGCAGTGGCGCACCTGGGCGTCGTGCTTCATCCA

GGCCGCGTGGAGAAGGTACGAGAAGCGGAAGGCGGCGGAGCATCGGAGGC

GAGAGGAGGAAGAGATGTACGCCGCCGAGATGGTGTCTGCGTCGTCGTCG

AGCCAGATCAAGACAGCGTTCCTCGTGTCGAGGTTCGCCAAGAATGCCAT

GCGCGGTGTGCAACGCCAGCGGTCGCACCAGGAGGAGAGGCTCATTCTGC

TGCCCAAGCCAAAAGACTAA

II. Reverse Transcription-Polymerase Chain Reaction (RT-PCR) Detection of TaCNGC5.1 Expression Induced by *Puccinia striiformis* f. Sp. *Tritici.*

1. Preparation of Experimental Materials

*P. striformis* f. sp. *tritici* inoculation was performed according to the method of Zhensheng Kang et al. (1984, Journal of Northwest A & F University). The leaves of suwon 11 were inoculated with CYR23, a incompatible race of stripe rust fungus, or CYR31, an compatible race of stripe rust fungus, to form a combination of incompatible and compatible interactions, and leaves inoculated with sterile water were used as a control.

Samples in the treatment groups were taken at 0 h, 6 h, 12 h, 24 h, 48 h, 72 h, 96 h, and 120 h after inoculation, respectively, and the same for that in the control. For sampling, fresh leaves were cut, wrapped in tinfoil paper, snap-frozen in liquid nitrogen, and then stored at −80° C. Total RNA of wheat leaves was extracted by Trizol method (TianGen), and the first strand cDNA was synthesized by reverse transcriptase XL (AMV). The cDNA was synthesized using the SMART method.

2, RT-PCR to Detect the Expression of TaCNGC5.1

Specific quantitative PCR primers were designed based on the sequences of wheat TaCNGC5.1 and the elongation factor TaEF-1α (GenBank accession number: U76744). RT-PCR Primer Sequences were:

QTaCNGC5.1-F:
(SEQ ID NO: 5)
5'-GCGGCCACCAGATGGACAGCTACTT-3';

QTaCNGC5.1-R:
(SEQ ID NO: 6)
5'-TCTTAAGGTCCTCCTGGAAGACACG-3';

QTaEF-F:
(SEQ ID NO: 7)
5'-TGGTGTCATCAAGCCTGGTATGGT-3';

QTaEF-R:
(SEQ ID NO: 8)
5'-ACTCATGGTGCATCTCAACGGACT-3'.

Quantitative PCR primers were tested for the specificity of their amplification products and amplification efficiency (>90%) before use, and TaEF-1α was used as an internal reference gene in Real-time PCR analysis. Real-time quantitative PCR amplification was performed using AceQ Universal SYBR qPCR Master Mix (Vazyme, Nanjing, China) and Bio-Rad CFX Manager quantitative PCR instrument (Bio-rad, Hercules, California), following the instructions with the cDNAs of the sampling points of each treatment as templates, respectively. At least 3 replicates were set for each reaction, and the Ct values for each replicate, as well as their mean and standard deviation, were generated by the quantitative PCR instrument by manually adjusting the baseline. Three replicates were set for each reaction, the Ct values were averaged, and the experimental data were analyzed by Delta Delta Ct method to determine the relative expression of the genes.

The results of quantitative RT-PCR (qRT-PCR) of TaCNGC5.1 in suwon 11 after inoculation with stripe rust incompatible race CYR23 and stripe rust compatible race CYR31, respectively, are shown in FIG. 1. As can be seen in FIG. 1, TaCNGC5.1 showed up-regulated expression in the pre-infestation stage after inoculation in both incompatible and compatible interations, suggesting that TaCNGC5.1 expression was induced by stripe rust fungus.

III. TaCNGC5.1 Subcellular Localization Analysis

1. Vector Construction

The PCR product TaCNGC5.1 fragment amplified in "I. Isolation of mRNA and amplification of TaCNGC5.1" was ligated into GFP16318 (green fluorescent protein) vector after BamH I digestion, to obtain the recombinant vector TaCNGC5.1-GFP, which expresses the fusion protein TaCNGC5.1-GFP.

The primer sequences for TaCNGC5.1-GFP used for subcellular localization of TaCNGC5.1 were as follows (underline indicates the cleavage site of BamH I):

```
TaCNGC5.1-GFP-F (SEQ ID NO: 9):
5'-TATCTCTAGAGGATCC ATGGACGGCCCCGGCAGCGGCCACC-3'.

TaCNGC5.1-GFP-R (SEQ ID NO: 10):
5'-TGCTCACCATGGATCC GTCTTTTGGCTTGGGCAGCAGAATG-3'.
```

2. Preparation of Protoplasmic System

Methods for Preparing Wheat Protoplasts for Transformation:

(1) Suwon 11 was broadcast and cultivated in soil-cultivating chamber.

(2) Under good growth conditions, leaves were taken before flowering to prepare protoplasts.

(3) Well-grown leaves were cut in the center and sliced into 0.5-1 mm wide strips with a razor blade.

(4) The cut leaf strips were placed in the pre-prepared cellulose solution shown in Table 2, approximately 10-20 leaves per 5-10 ml of solution. The leaves were pressed with tweezers for complete immerse in the solution.

(5) Vacuum pumping was conducted in the dark (with the leaves wrapped in tin foil) for 30 minutes. The PEG4000 solution shown in Table 3 was prepared, and the 200 ul and 1000 μl scaled pipette tips were de-tipped to ease pipetting during operation.

(6) The resulting product was allowed for standing at room temperature without shaking, and then digested continuously under dark conditions at 28° C. 50 rpm with shaking for at least 3 h. When the solution turns green, the petri dish was gently shaken to facilitate the release of protoplasts.

(7) Protoplasts in solution were examined under a microscope; and wheat mesophyll protoplasts were about 30-50 μm in size.

(8) The solution containing protoplasts with an equal amount of the W5 solution shown in Table 4 (pre-cooled) was diluted before filtering to remove undissolved leaves.

(9) A 35-75 μm nylon membrane or 60-100-mesh sieve was first moistened with W5 solution and then used to filter the solution containing protoplasts.

(10) The protoplasts were precipitated by centrifugation at 100 g in a 30 ml round-bottomed centrifuge tube for 1-2 min at 4° C., and the supernatant was removed as much as possible. The protoplasts were then gently resuspended with 10 ml of pre-cooled W5 solution on ice.

(11) The protoplasts were rested on ice for 30 minutes.

The following operations were performed at room temperature of 23° C.

(12) The protoplasts were precipitated by centrifuge at 100 g for 8-10 min. The W5 solution was removed as much of as possible without contacting the protoplasmic precipitates. The protoplasts were then resuspended with an appropriate amount of MMG solution (1 mL) to give a final concentration of $2\times10^5$ protoplasts/ml.

(13) 10 μl or 20 ul of DNA (10-20 μg of approximately 5-10 kb of recombinant vector TaCNGC5.1-GFP) was added to a 2 ml EP tube.

(14) 100 μl of protoplasts ($2\times10^4$ units) were added and mixed gently.

(15) 110 μl of PEG solution was added and the centrifuge tube was gently tapped to allow complete mixing (approximately 6-10 samples can be transformed at a time).

(16) Induction of the transformation mixture was performed for 20-30 min (transformation time depends on the experiment, and longer transformation time may be needed for higher expression).

(17) The transformation was terminated by diluting the transformed mixture with 400-440 μl of W5 solution at room temperature and the centrifuge tube was then gently inverted and shaken to allow complete mixing.

(18) Centrifuge was carried out at 100 g for 2 min at room temperature, and then the supernatant was removed. 1 ml of W5 solution suspension was added for washing once, centrifuge was performed at 100 g for 2 min to remove the supernatant.

(19) The protoplasts were gently resuspended with 1 ml of WI solution in a multiwell tissue culture plate.

(20) The protoplasts were induced at room temperature (20-25° C.) for more than 18 hours.

Protoplasts transfected with GFP16318 vector was used as a control.

Afterwards, GFP tag expression was observed under a laser confocal microscope.

3. Microscopy of Wheat Protoplast:

Protoplasts after 18 h of dark culture were pressed into slices, and then GFP (green fluorescent protein) fluorescence was observed in a laser scanning confocal microscope (LSMC, Biorad MicroRadiance) and scanned and photographed. The working parameters of the LSCM were Ex=488 nm, Em=525±15 nm, Power=10%, Zoom 7, Medium speed scanning, Frame512×512. The software was TIME-COURSE and PHOTOSHOP5.0.

Figure 2:
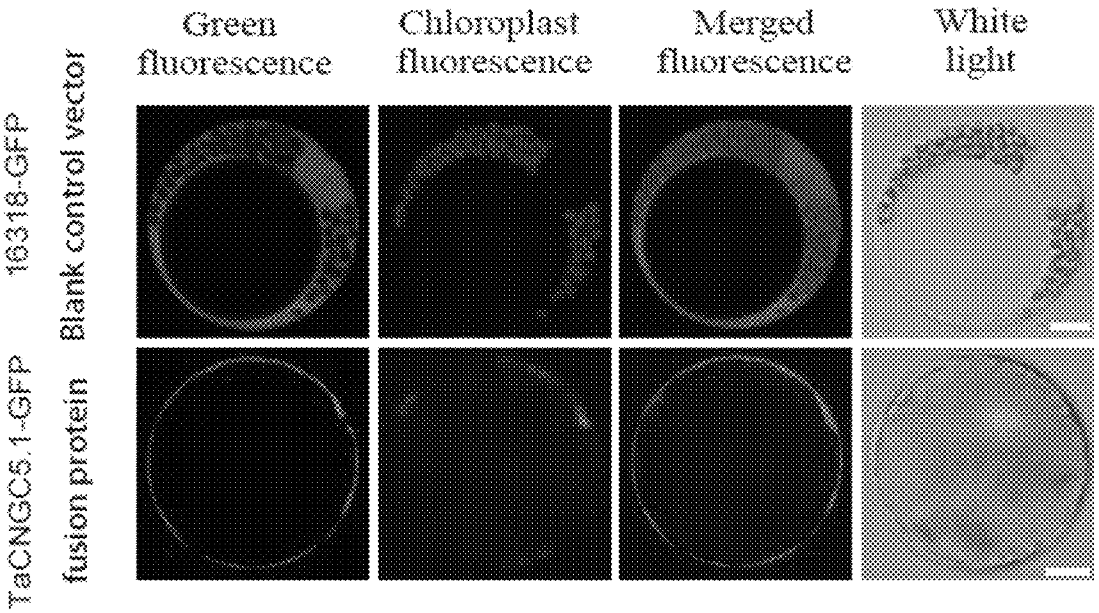
FIG. 2 shows the results of TaCNGC5.1 localization in wheat protoplasts.

The results are shown in FIG. 2 (scale bar=10 μm), and the upper one is the control protoplasts (16318-GFP) transfected with GFP16318 empty vector; the lower one is the localization of TaCNGC5.1 in protoplasts transfected with recombinant vector TaCNGC5.1-GFP (TaCNGC5.1-GFP). As can be seen from the FIG. 2 that TaCNGC5.1 localizes in the cell membrane.

Example 2: Use of TaCNGC5.1 Gene in Improving Resistance to Stripe Rust in Plants I. Acquisition of Wheat Transformed with TaCNGC5.1 Gene 1. Construction of TaCNGC5.1 Gene Overexpression Vector The CUB vector is described in "Shuzhang Xie, Kairong Lei, Xiaoyan Yang et al. Study on insect-resistant gene of GmCry1F transformation in maize by *Agrobacterium*-mediated [J]. Southwest China Journal of Agricultural Sciences, 2015, 28(3):962-966" and is available to the public from Northwest A&F University.

TaCNGC5.1-CUB Vector was Specifically Constructed as Follows:

PCR amplification was carried out with TaCNGC5.1-CUB-F and TaCNGC5.1-CUB-R as primers, and TaCNGC5.1 full-length CDS amplified in the first part of Example 1 as a template, and the amplified fragment (nucleotides 1-2067 of SEQ ID NO: 2 in the Sequence listing) was constructed into a BamH I digested CUB vector by homologous recombination using ClonExpress II One Step Cloning Kit (vazyme) to obtain the recombinant vector TaCNGC5.1-CUB, which is a recombinant vector obtained by inserting the sequence of nucleotides 1-2067 of SEQ ID NO:2 in the sequence listing into the CUB vector, with the rest of the bases remained unchanged.

```
TaCNGC5.1-CUB-F (SEQ ID NO: 11):
5'-CAGGTCGACTCTAGAGGATCCATGGACGGCCCCGGCAGCGGCCACC-
3'

TaCNGC5.1-CUB-R (SEQ ID NO: 12):
5'-GAGCTCGGTACCCGGGGATCCGTCTTTTGGCTTGGGCAGCAGAATG-
3'.
```

Note: the underline indicates the enzyme cleavage site of BamH I.

2. Acquisition of Wheat Transformed with TaCNGC5.1 Gene

The recombinant vector TaCNGC5.1-CUB was used to infect the callus of wild-type wheat Fielder using *Agrobacterium* to obtain TO generation of TaCNGC5.1 transgenic wheat. The TO generation TaCNGC5.1 transgenic wheat was cultivated until two lines of T3 generation TaCNGC5.1 transgenic wheat were obtained.

3. PCR Validation

Genomic DNA from leaves of two lines of T3 generation TaCNGC5.1 transgenic wheat for and wild-type control (Fielder) were extracted separately using CTAB, and TaCNGC5.1 overexpression assay primers (F/R) were utilized to verify whether the aforementioned plants were transgene-positive plants.

```
F:
                    (SEQ ID NO: 13)
TGGGGTCTCCAGAACCTCAGCAGTG;

R:
                    (SEQ ID NO: 14)
AATTGCGGGACTCTAATCATA.
```

Molecular assays were performed on T3 generation transgenic plants (upstream primer F is located on the TaCNGC5.1 gene and downstream primer R is located on the NOS terminator). Water was used as a blank control. Ten plants were randomly taken from each line.

Figure 3A:
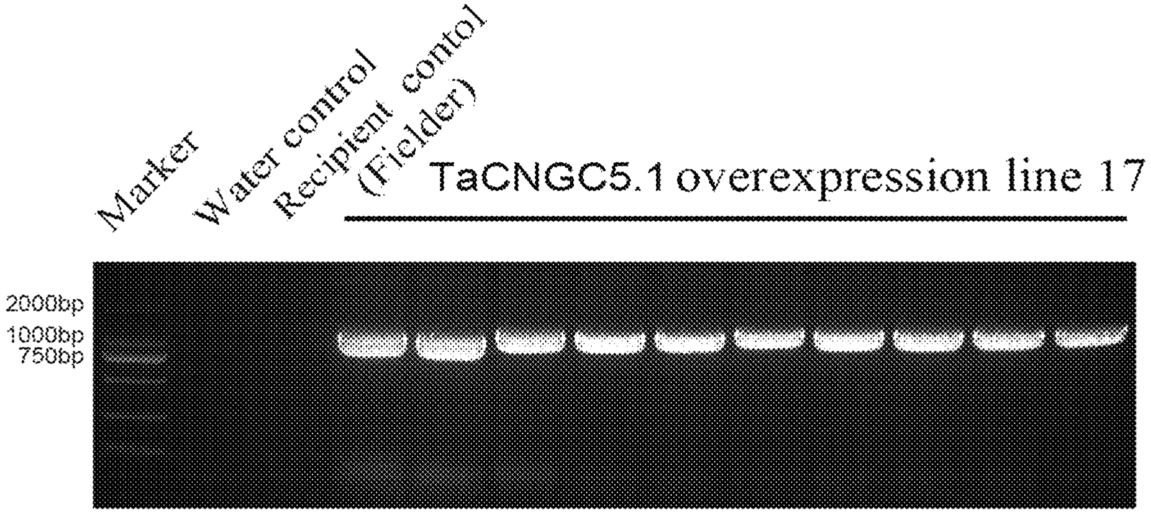
FIGS. 3A-3B show the results of Polymerase Chain Reaction (PCR) identification of TaCNGC5.1 overexpressing wheat T3 generation.
Figure 3B:
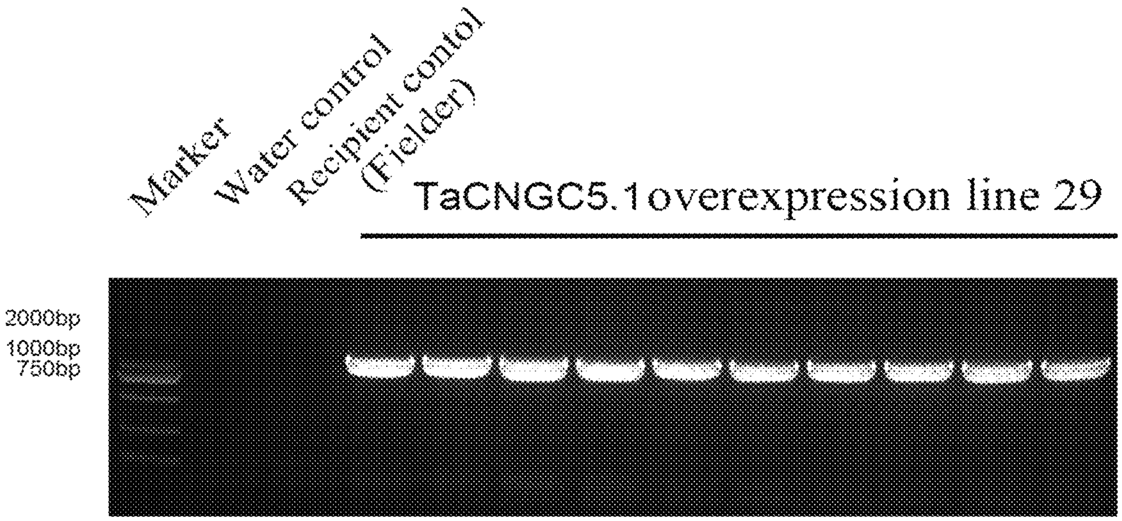

The results are shown in FIGS. 3A-3B. Plants with DNA fragments of approximately 2000-1000 bp in the PCR products were positive lines, and both T3 generation lines overexpressing TaCNGC5.1 (TaCNGC5.1 overexpressing line 17 and TaCNGC5.1 overexpressing line 29) were positive lines, named as TaCNGC5.1 overexpressing line 17, and TaCNGC5.1 overexpression line 29, respectively.

II. Analysis of Stripe Rust Resistance in TaCNGC5.1 Transgenic Wheat

Wild-type wheat Fielder, TaCNGC5.1 overexpression line 17 and TaCNGC5.1 overexpression line 29 were planted in an incubator at 25/23° C. with day/night temperature and 16 h light/8 h dark photoperiod. After the second leaf unfolded (FIG. 4A), the plants were inoculated with CYR31, CYR32, CYR33, and CYR34, respectively, and the inoculation methods were described in "Zhensheng Kang, Zhenqi Li. Discovery of a normal T. type of new pathogenic strain Lovrin 10[J]. Journal of Northwest A & F University (Natural Science Edition), 1984 (04):18-28". Leaves from the inoculation site were taken as RNA extraction samples 120 hours after inoculation, and the pathogenic phenotype was observed at 14 d after inoculation. Data were processed using Graphpad Prism 8.3.0, and the results were expressed as mean±standard deviation, with two-tailed t-tests of $P<0.05$. (*) stands for significant differences and $P<0.01$ (**) stands for highly significant differences.

Figure 4A:
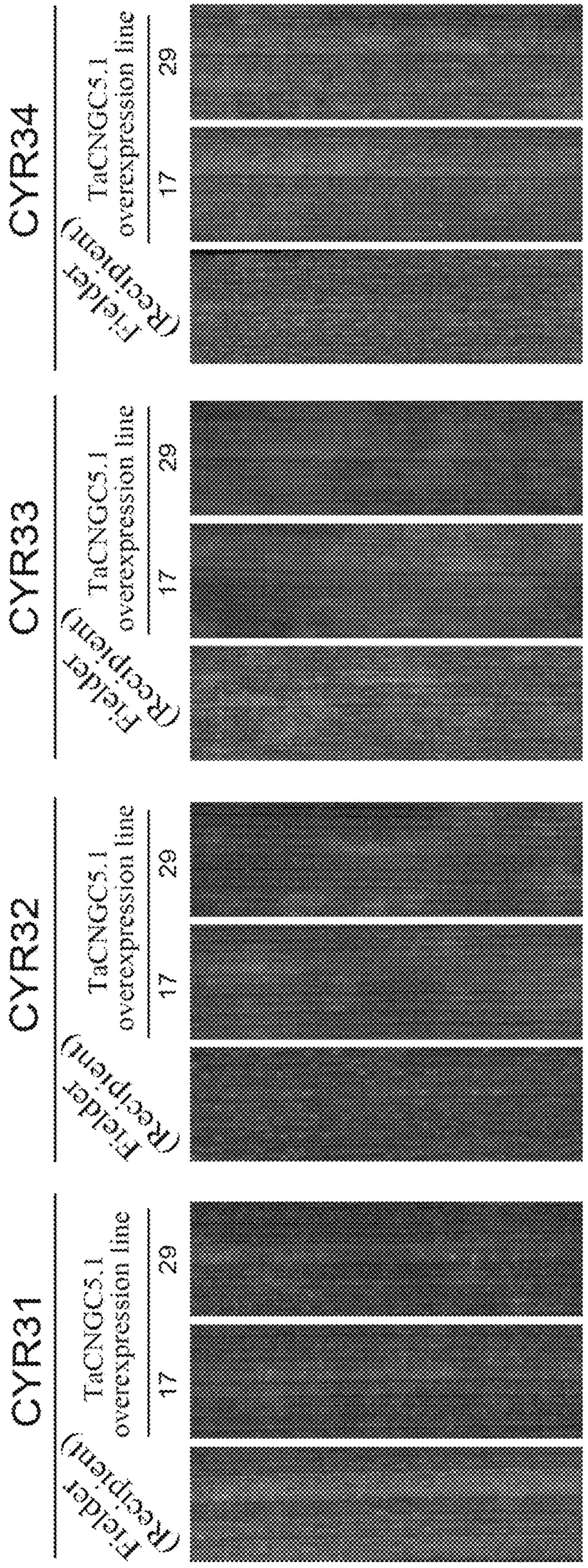
FIGS. 4A-4C show the disease resistance identification TaCNGC5.1 transgenic wheat (CYR31, CYR32, CYR33 and CYR34).
Figure 4B:
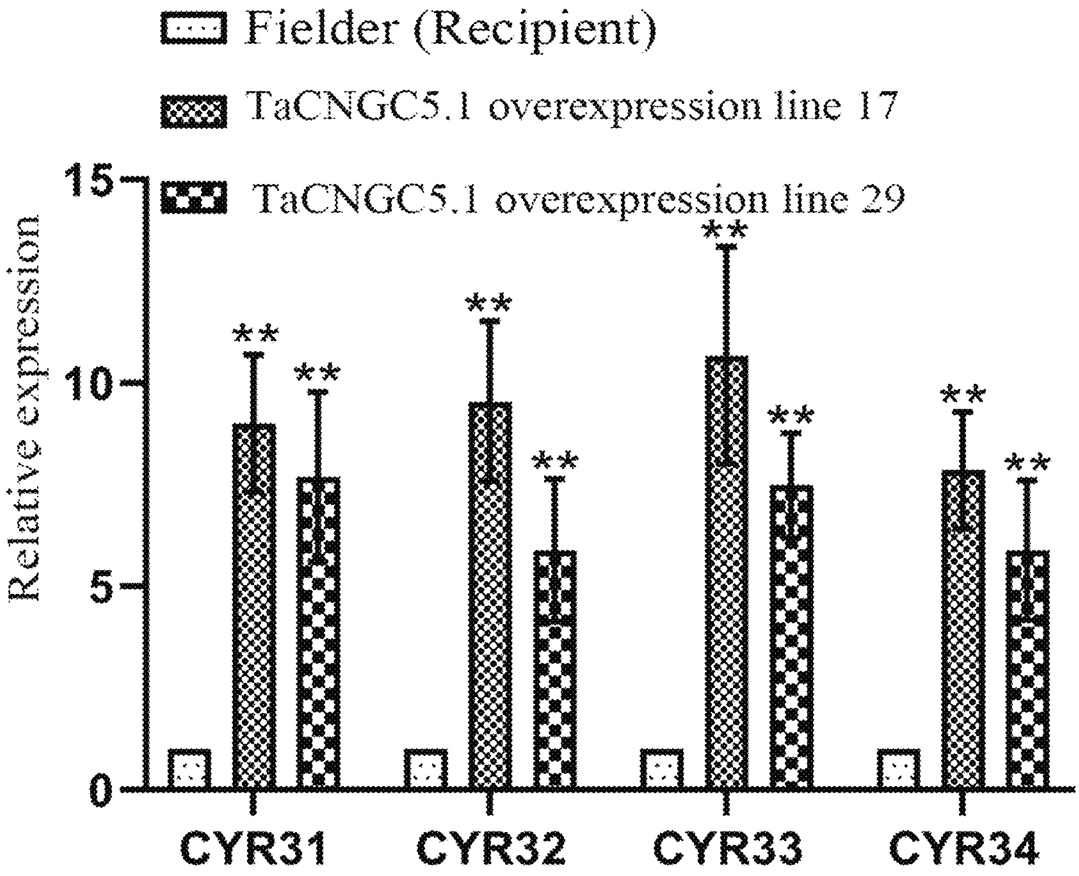

The phenotypic results are shown in FIG. 4A. Under the conditions of stripe rust CYR31, CYR32, CYR33, and CYR34 infestation, a large number of uredinia were observed on the leaves of all treatments of wild-type wheat Fielder of the control plants, whereas the number of uredinia on the TaCNGC5.1 overexpression line 17 and the TaCNGC5.1 overexpression line 29 leaves was significantly reduced, and the area of fading green necrosis area increased. The expression of TaCNGC5.1 in wild-type wheat, TaCNGC5.1 overexpressing line 17, and TaCNGC5.1 overexpressing line 29 during the process of stripe rust infestation was also detected as in the RT-PCR assay of Example 1, with RNA from samples 120 h after different inoculations as a template. The results are shown in FIG. 4B. TaCNGC5.1 expression in the overexpression materials was consistently more than 5-fold higher than the control.

3. Biomass Assay

Stripe rust fungi biomass was measured in wheat 14 days after inoculation with Stripe rust fungi. The biomass assay was performed according to "Tuo Qi, Jia Guo, Peng Liu, Fuxin He, Cuiping Wan, Md Ashraful Islam, Brett M Tyler, Zhensheng Kang, Jun Guo, Stripe Rust Effector PstGSRE1 Disrupts Nuclear Localization of ROS-Promoting Transcription Factor TaLOL2. Effector PstGSRE1 Disrupts Nuclear Localization of ROS-Promoting Transcription Factor TaLOL2 to Defeat ROS-Induced Defense in Wheat. Mol. Plant. 2019 Dec. 2; 12(12):1624-1638."

Figure 4C:
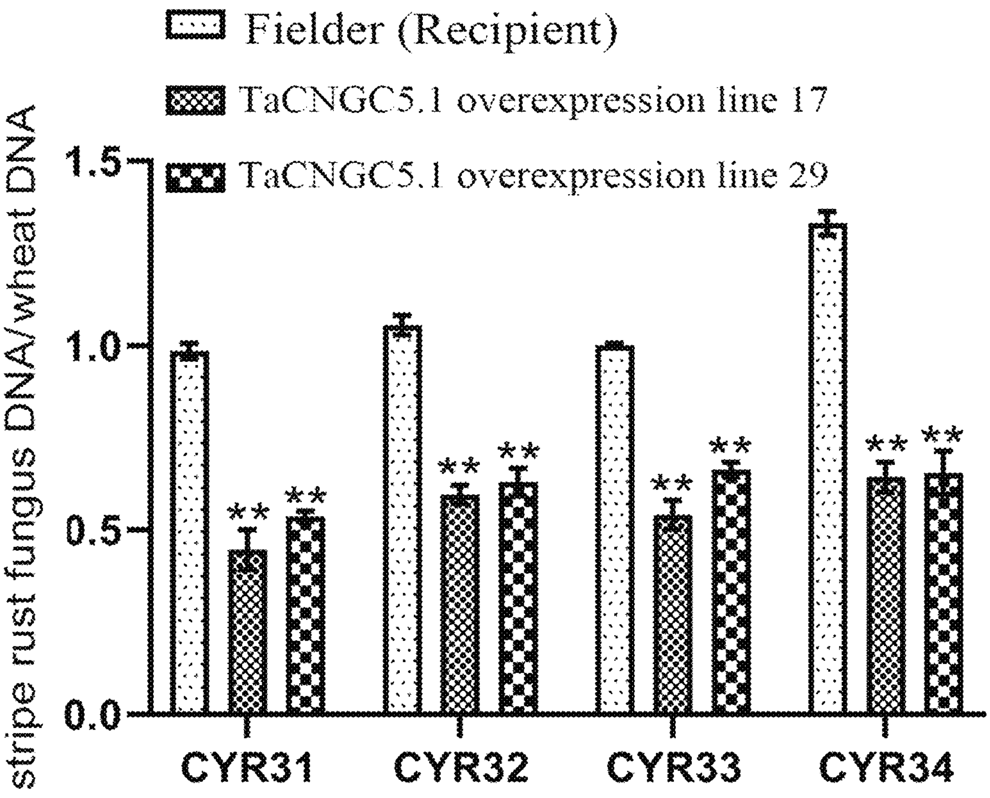

The results are shown in FIG. 4C. It was found that the biomass of stripe rust fungi was significantly reduced in overexpressing wheat (FIG. 4C).

The above results of disease resistance characterization indicated that under the treatments of four physiological races, CYR31, CYR32, CYR33 and CYR34, TaCNGC5.1 transgenic wheat showed strong resistance. This is a verified advantage in production.

It is shown that TaCNGC5.1 is an important gene involved in the response process of stripe rust resistance in wheat.

The present disclosure is described in detail as above. For those skilled in the art, the present disclosure may be practiced in a wide range of equivalent parameters, concentrations and conditions without departing from the purpose and scope of the present disclosure and without undue experimentation. Although particular embodiments of the present disclosure are given, it should be understood that further improvements can be made to the present disclosure. In summary, in accordance with the principles of the present disclosure, the present application is intended to include any modifications, uses or changes to the present disclosure, including changes that are out of the scope of what has been disclosed in the present application using conventional techniques known in the art.

What is claimed is:

1. A method for breeding transgenic wheat with improved resistance to stripe rust, the method comprising transforming a target wheat plant with an expression cassette comprising a gene having the coding sequence of SEQ ID NO: 2 to obtain a disease-resistant wheat plant having a higher resistance to stripe rust than that of the target wheat plant, wherein the gene encodes a protein having the amino acid sequence of SEQ ID NO: 1.

* * * * *

SEQUENCE LISTING

```
Sequence total quantity: 19
SEQ ID NO: 1            moltype = AA  length = 689
FEATURE                 Location/Qualifiers
source                  1..689
                        mol_type = protein
                        note = TaCNGC5.1
                        organism = Triticum aestivum
SEQUENCE: 1
MDGPGSGHQM DSYFSRAPKI RSRSIRMAAA GVMSQSERLK NIGRRVFQED LKSISLKIYD  60
PQDPFLMRMN RLFVFACIIS VATDPLFFYL PSVNVTQSNT CIGFKRELAV AATAVRTAID  120
FFYLARIVLQ FHTAFIAPSS RVFGRGELVV DHGDIARRYL RRFFVVDLLS VLPLPQIQMY  180
KFFMKPKNAD LLPVKTALFF NVLTQYLPRL LRFYPITAEL RRTTGVFAET ALSGAAFYLL  240
LYMLCSHMVG SFWYLLAVER LDDCWREKCA GLKFHQCRIY MYCGGKQEGD EDDFMKWRTM  300
IRQVLAQECA PVDNNGTGFS YGIYTSAMTS GVTHTNDLVP KILYCLWWGL QNLSSGAQGL  360
ETTHYKGEAL FAIILAVFGL ILMALLIGNM QTYLQSMTLR MEEMRLKRRD SEEWMRHRDL  420
PDDLRERVWR HNQYKWLETR GVDEDGLVSC LPKDIRRDVK RHLCLRLVRR VPLFANMDER  480
LLDAICERLK PSLCTETTYV VREGEPVDEM LFIIRGRLES STTDGGRTGF FNKGLLKEGD  540
FCGEELLTWA LDPKAAANLP LSTRSVKALS EVEGFALHAD ELKFVAGQFR RLHSKQLQQT  600
FRFYSQQWRT WASCFIQAAW RRYEKRKAAE HRRREEEEMY AAEMVSASSS SQIKTAFLVS  660
RFAKNAMRGV QRQRSHQEER LILLPKPKD                                  689

SEQ ID NO: 2            moltype = DNA  length = 2070
FEATURE                 Location/Qualifiers
source                  1..2070
                        mol_type = other DNA
                        note = DNA encoding the TaCNGC5.1 protein
                        organism = Triticum aestivum
SEQUENCE: 2
atggacggcc ccggcagcgg ccaccagatg gacagctact tctcccgcgc ccccaagatc  60
cggtcccggt ccatccgcat ggcggctgcc ggcgtgatga gccagtcgga gcggctcaag  120
aacatcgggc gccgtgtctt ccaggaggac cttaagagca tctccctcaa gatctacgac  180
ccgcaggacc cgttcctgat gcgcatgaac cgcctcttcg tcttcgcctg catcatctcc  240
gtcgccaccg acccgctctt cttctacctc ccttccgtca acgtgaccca gagcaacaca  300
tgcatcggct tcaaacgtga actggccgtc gctgccaccg ctgtgcgcac cgccatcgac  360
ttcttctacc tggcgcggat cgtgctgcag ttccacaccg ccttcatcgc gccgtcgtcg  420
cgggtgtttg gccgcgggga gctcgtcgtc gaccatggtg acatagcgcg ccgctacctc  480
cgccgttttt tcgtcgtcga cctcctctct gtgctccccc tgccacaaat ccagatgtac  540
aagttcttca tgaagcccaa gaacgcggac ctgcttcccg tcaagacggc gctcttcttc  600
aacgtactca cccagtactt gccccgcctc ctccgcttct accctatcac cgccgaactc  660
aggcgcacca ccggcgtctt cgcagagact gccttatccg gcgccgcctt ctacctcctc  720
ctctacatgc tatgctcaca catggtgggt tccttctggt acctcctcgc cgtcgagcgc  780
ctcgacgact gctggcgcga gaagtgcgcg gggctcaagt tccaccagtg caggatatac  840
atgtactgcg gggggaaaca agagggcgat gaggacgact tcatgaagtg gcggaccatg  900
atccggcagg tgctcgcgca ggagtgcgcg cctgtggaca acaacggcac gggcttcagc  960
tacggcatct acacctccgc catgacctca ggggtcaccc acaccaacga cctcgtcccg  1020
aagattctct actgcctgtg gtggggtctc cagaacctca gcagtggcgc ccaggggctg  1080
gagaccacgc actacaaggg ggaggccctt ttcgccatca tcctcgcggt cttcggcctc  1140
atcctcatgg cgctgctcat cggcaacatg cagacgtacc tccagtccat gacgctgcgt  1200
atggaggaga tgcggctcaa gcggcgggac tcggaggagt ggatgcgcca tcgcgacctc  1260
cccgatgacc tccgggagcg tgtgtggcga cacaaccagt acaagtggct ggagacgcgg  1320
ggcgtggacg aggacggcct tgtgagctgc ctccccaagg acatccggcg agacgtcaag  1380
cgccacctct gcctccgcct cgtccgccgc gtgccgctct ttgccaacat ggacgagcgc  1440
ctcctcgacg ccatctgcga gaggctcaag cccagcctat gcacggagac cacctacgtg  1500
gtgcgggaag ggagcccgt cgacgagatg ctcttcatca tcagaggccg gctcgagagt  1560
tccaccaccg acgggggccg cacggggttc ttcaacaagg ggctcctcaa ggaaggggac  1620
ttctgcggcg aggagctcct cacatgggcg ctggacccaa aggctgcggc gaacctgccg  1680
ctgtccactc gtagtgtcaa ggcgctctcc gaggtggagg gcttcgcgct gcacgccgat  1740
gagcttaagt tcgtcgcggg gcagttccgg cgcctgcaca gcaagcaatt gcagcagacc  1800
ttcaggttct actcgcagca gtggcgcacc tgggcgtcgt gcttcatcca ggccgcgtgg  1860
agaaggtacg agaagcggaa ggcggcggag catcggaggc gagaggagga agagatgtac  1920
gccgccgaga tggtgtctgc gtcgtcgtcg agccagatca agacagcgtt cctcgtgtcg  1980
aggttcgcca agaatgccat gcgcggtgtg caacgccagc ggtcgcacca ggaggagagg  2040
ctcattctgc tgcccaagcc aaaagactaa                                 2070

SEQ ID NO: 3            moltype = DNA  length = 25
FEATURE                 Location/Qualifiers
source                  1..25
                        mol_type = other DNA
                        note = Primer TaCNGC5.1-F
                        organism = synthetic construct
SEQUENCE: 3
atggacggcc ccggcagcgg ccacc                                      25

SEQ ID NO: 4            moltype = DNA  length = 25
FEATURE                 Location/Qualifiers
source                  1..25
                        mol_type = other DNA
                        note = Primer TaCNGC5.1-R
```

```
                         organism = synthetic construct
SEQUENCE: 4
ttagtctttt ggcttgggca gcaga                                25

SEQ ID NO: 5             moltype = DNA  length = 25
FEATURE                  Location/Qualifiers
source                   1..25
                         mol_type = other DNA
                         note = Primer QTaCNGC5.1-F
                         organism = synthetic construct
SEQUENCE: 5
gcggccacca gatggacagc tactt                                25

SEQ ID NO: 6             moltype = DNA  length = 25
FEATURE                  Location/Qualifiers
source                   1..25
                         mol_type = other DNA
                         note = Primer QTaCNGC5.1-R
                         organism = synthetic construct
SEQUENCE: 6
tcttaaggtc ctcctggaag acacg                                25

SEQ ID NO: 7             moltype = DNA  length = 24
FEATURE                  Location/Qualifiers
source                   1..24
                         mol_type = other DNA
                         note = Primer QTaEF-F
                         organism = synthetic construct
SEQUENCE: 7
tggtgtcatc aagcctggta tggt                                 24

SEQ ID NO: 8             moltype = DNA  length = 24
FEATURE                  Location/Qualifiers
source                   1..24
                         mol_type = other DNA
                         note = Primer QTaEF-R
                         organism = synthetic construct
SEQUENCE: 8
actcatggtg catctcaacg gact                                 24

SEQ ID NO: 9             moltype = DNA  length = 41
FEATURE                  Location/Qualifiers
source                   1..41
                         mol_type = other DNA
                         note = Primer TaCNGC5.1-GFP-F
                         organism = synthetic construct
SEQUENCE: 9
tatctctaga ggatccatgg acggccccgg cagcggccac c              41

SEQ ID NO: 10            moltype = DNA  length = 41
FEATURE                  Location/Qualifiers
source                   1..41
                         mol_type = other DNA
                         note = Primer TaCNGC5.1-GFP-R
                         organism = synthetic construct
SEQUENCE: 10
tgctcaccat ggatccgtct tttggcttgg gcagcagaat g              41

SEQ ID NO: 11            moltype = DNA  length = 46
FEATURE                  Location/Qualifiers
source                   1..46
                         mol_type = other DNA
                         note = Primer TaCNGC5.1-CUB-F
                         organism = synthetic construct
SEQUENCE: 11
caggtcgact ctagaggatc catggacggc cccggcagcg gccacc         46

SEQ ID NO: 12            moltype = DNA  length = 46
FEATURE                  Location/Qualifiers
source                   1..46
                         mol_type = other DNA
                         note = Primer TaCNGC5.1-CUB-R
                         organism = synthetic construct
SEQUENCE: 12
gagctcggta cccggggatc cgtcttttgg cttgggcagc agaatg         46

SEQ ID NO: 13            moltype = DNA  length = 25
FEATURE                  Location/Qualifiers
source                   1..25
```

-continued

```
                        mol_type = other DNA
                        note = Primer F
                        organism = synthetic construct
SEQUENCE: 13
tggggtctcc agaacctcag cagtg                                            25

SEQ ID NO: 14           moltype = DNA  length = 21
FEATURE                 Location/Qualifiers
source                  1..21
                        mol_type = other DNA
                        note = Primer R
                        organism = synthetic construct
SEQUENCE: 14
aattgcggga ctctaatcat a                                                21

SEQ ID NO: 15           moltype = AA  length = 5
FEATURE                 Location/Qualifiers
source                  1..5
                        mol_type = protein
                        note = Poly-Arg tag
                        organism = synthetic construct
SEQUENCE: 15
RRRRR                                                                  5

SEQ ID NO: 16           moltype = AA  length = 6
FEATURE                 Location/Qualifiers
source                  1..6
                        mol_type = protein
                        note = Poly-His tag
                        organism = synthetic construct
SEQUENCE: 16
HHHHHH                                                                 6

SEQ ID NO: 17           moltype = AA  length = 8
FEATURE                 Location/Qualifiers
source                  1..8
                        mol_type = protein
                        note = FLAG tag
                        organism = synthetic construct
SEQUENCE: 17
DYKDDDDK                                                               8

SEQ ID NO: 18           moltype = AA  length = 8
FEATURE                 Location/Qualifiers
source                  1..8
                        mol_type = protein
                        note = Strep-tag II
                        organism = synthetic construct
SEQUENCE: 18
WSHPQFEK                                                               8

SEQ ID NO: 19           moltype = AA  length = 10
FEATURE                 Location/Qualifiers
source                  1..10
                        mol_type = protein
                        note = c-myc tag
                        organism = synthetic construct
SEQUENCE: 19
EQKLISEEDL                                                             10
```